(12) United States Patent
Dickie et al.

(10) Patent No.: US 10,588,607 B2
(45) Date of Patent: Mar. 17, 2020

(54) SYSTEMS AND METHODS FOR MANAGING POWER IN AN ULTRASOUND IMAGING MACHINE

(71) Applicant: Clarius Mobile Health Corp., Burnaby (CA)

(72) Inventors: Kris Dickie, Vancouver (CA); Trevor Stephen Hansen, Vancouver (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 336 days.

(21) Appl. No.: 15/836,560

(22) Filed: Dec. 8, 2017

(65) Prior Publication Data
US 2019/0175149 A1    Jun. 13, 2019

(51) Int. Cl.
*A61B 8/00*      (2006.01)
*A61B 17/00*    (2006.01)

(52) U.S. Cl.
CPC .............. *A61B 8/56* (2013.01); *A61B 8/4254* (2013.01); *A61B 8/4427* (2013.01); *A61B 8/4444* (2013.01); *A61B 8/4472* (2013.01); *A61B 8/54* (2013.01); *A61B 17/00* (2013.01); *A61B 2560/0209* (2013.01); *A61B 2562/0219* (2013.01); *A61B 2562/0223* (2013.01)

(58) Field of Classification Search
CPC ........ A61B 8/56; A61B 8/4254; A61B 8/4427
See application file for complete search history.

(56) References Cited

U.S. PATENT DOCUMENTS

| | | |
|---|---|---|
| 5,517,994 A | 5/1996 | Burke et al. |
| 5,529,070 A | 6/1996 | Augustine et al. |
| 5,654,509 A | 8/1997 | Miele et al. |
| 5,996,083 A | 11/1999 | Gupta et al. |
| 6,126,598 A | 10/2000 | Entrekin et al. |
| 6,450,958 B1 | 9/2002 | Linkhart et al. |
| 6,471,651 B1 | 10/2002 | Hwang et al. |
| 6,477,654 B1 | 11/2002 | Dean et al. |
| 6,527,719 B1 | 3/2003 | Olsson et al. |
| 6,527,721 B1 | 3/2003 | Wittrock et al. |
| 6,542,846 B1 | 4/2003 | Miller et al. |
| 6,592,521 B1 | 7/2003 | Urbano et al. |
| 6,610,011 B2 | 8/2003 | Emery |
| 6,697,953 B1 | 2/2004 | Collins |
| 7,338,446 B2 | 3/2008 | MacDonald et al. |
| 7,371,218 B2 | 5/2008 | Walston et al. |
| 7,383,457 B1 | 6/2008 | Knight |
| 7,984,651 B2 | 7/2011 | Randall et al. |

(Continued)

FOREIGN PATENT DOCUMENTS

WO       2009065167 A1     5/2009

*Primary Examiner* — Joseph M Santos Rodriguez
(74) *Attorney, Agent, or Firm* — Julian Ho

(57) ABSTRACT

The present embodiments relate generally to managing power in an ultrasound imaging machine. The ultrasound imaging machine may generate ultrasound images while operating in a first imaging mode that consumes power at a first level. The ultrasound imaging machine may determine whether the generated ultrasound images are for viewing. If generated ultrasound images are not for viewing, the ultrasound imaging machine may change to a second imaging mode that consumes power at a second level less than the first level. If ultrasound images generated while operating in the second imaging mode are not for viewing, the ultrasound imaging machine may change to a freeze mode that consumes power at a third level less than the second level.

20 Claims, 6 Drawing Sheets

(56) References Cited

U.S. PATENT DOCUMENTS

| | | |
|---|---|---|
| 7,996,688 B2 | 8/2011 | Little |
| 8,079,263 B2 | 12/2011 | Randall et al. |
| 8,417,979 B2 | 4/2013 | Maroney |
| 8,461,978 B2 | 6/2013 | Garner et al. |
| 8,568,325 B2 | 10/2013 | Moritz |
| 9,204,860 B2 | 12/2015 | Ji et al. |
| 2002/0082501 A1 | 6/2002 | Emery |
| 2005/0251045 A1 | 11/2005 | MacDonald et al. |
| 2006/0058652 A1 | 3/2006 | Little |
| 2008/0114247 A1 | 5/2008 | Urbano et al. |
| 2008/0114249 A1 | 5/2008 | Randall et al. |
| 2008/0208051 A1 | 8/2008 | Choi |
| 2009/0043203 A1 | 2/2009 | Pelissier et al. |
| 2009/0150692 A1 | 6/2009 | Poland |
| 2010/0262012 A1 | 10/2010 | Wu |
| 2010/0277305 A1 | 11/2010 | Garner et al. |
| 2013/0083629 A1 | 4/2013 | Ji et al. |
| 2015/0245823 A1 | 9/2015 | Jin et al. |

…

SYSTEMS AND METHODS FOR MANAGING POWER IN AN ULTRASOUND IMAGING MACHINE

FIELD

The present disclosure relates generally to ultrasound imaging, and in particular, to systems and methods for managing power in an ultrasound imaging machine.

BACKGROUND

Ultrasound imaging systems are a powerful tool for performing real-time, non-invasive imaging procedures in a wide range of medical applications. An ultrasound machine includes a transducer which sends out ultrasound signals into tissue. Ultrasound waves are reflected back from the tissue and are received by the transducer. The reflected echo signals are processed to produce an ultrasound image of the target anatomy. An ultrasound machine typically has a user input device by which the operator of the ultrasound machine can control the machine to obtain images of tissue structures.

To make ultrasound imaging machines more portable and ergonomic, the traditionally large cart-based machines have been replaced with smaller, battery-powered devices. With limited power capacity, careful power management is required to achieve an optimal balance between generating high quality images, maximizing scanning time, and/or limiting heat generation.

While a variety of power reduction techniques are described in the art, there remains a need for improved systems and methods for balancing power consumption and performance. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
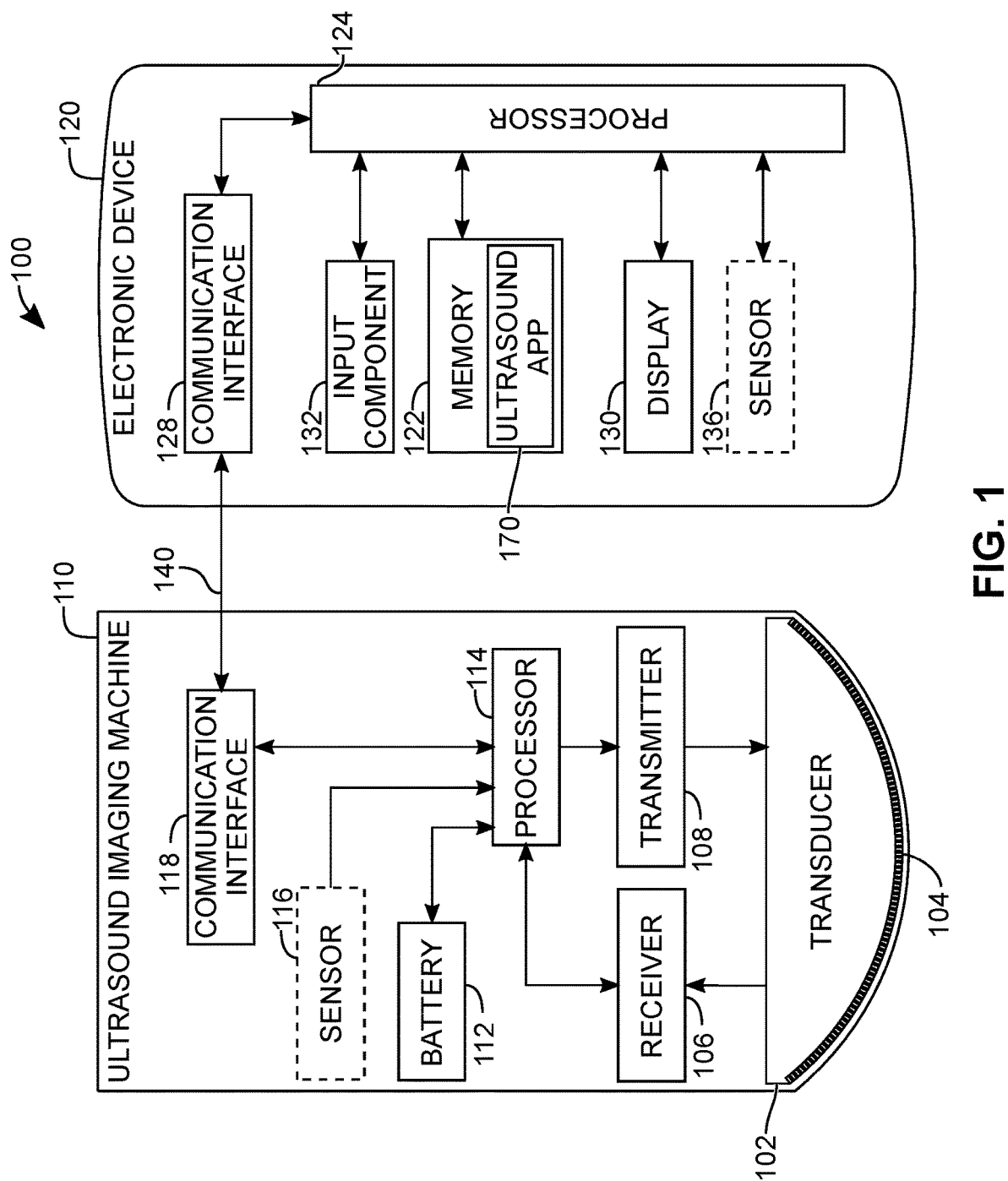
FIG. 1 shows a functional block diagram of an ultrasound system, according to at least one embodiment of the present disclosure.

In a first broad aspect of the present disclosure, there is provided a method of managing power consumption in an ultrasound imaging machine, the method involving: operating the ultrasound imaging machine in a first imaging mode to generate at least one first ultrasound image, wherein the first imaging mode consumes power at a first power level; determining whether the at least one first ultrasound image generated in the first imaging mode is for viewing; if determined that the at least one first ultrasound image generated in the first imaging mode is not for viewing, changing from the first imaging mode to a second imaging mode that consumes power at a second power level, wherein the second power level is lower than the first power level; operating the ultrasound imaging machine in the second imaging mode to generate at least one second ultrasound image; determining whether the at least one second ultrasound image generated in the second imaging mode is for viewing; and if determined that the at least one second ultrasound image generated in the second imaging mode is not for viewing, changing from a second imaging mode to a freeze mode that consumes power at a third level, wherein the third power level is lower than the second power level.

In some embodiments, determining whether the at least one first ultrasound image generated in the first imaging mode is for viewing involves determining if the ultrasound imaging machine has been inactive for longer than a first time period, and determining whether the at least one second ultrasound image generated in the second imaging mode is not for viewing involves determining if the ultrasound imaging machine has been inactive for longer than a second time period.

In some embodiments, at least one of the first time period and the second time period is user configurable.

In some embodiments, a frame rate of imaging involves the time between a first transmit sequence and a second transmit sequence, and changing from the first imaging mode to the second imaging mode involves reducing the frame rate of imaging.

In some embodiments, changing from the first imaging mode to the second imaging mode involves reducing a transmit amplitude of ultrasound pulses transmitted from the ultrasound imaging machine.

In some embodiments, determining whether the at least one first ultrasound image generated in the first imaging mode is for viewing involves analyzing the at least one first ultrasound image.

In some embodiments, determining whether the at least one first ultrasound image generated in the first imaging mode is for viewing involves reading a motion sensor. In some embodiments, the motion sensor includes at least one of an accelerometer, a magnetometer, and a gyroscope.

In some embodiments, changing from the first imaging mode to the second imaging mode involves disabling an advanced imaging processing mode. In some embodiments, the advanced imaging processing mode involves at least one of: spatial compounding, synthetic aperture, and dual focus.

In some embodiments, the method further involves: operating the ultrasound imaging machine in the freeze mode; determining whether the ultrasound imaging machine has resumed imaging; and if determined that the ultrasound imaging machine has not resumed imaging, changing from a freeze mode to an idle mode that consumes power at a fourth level, wherein the fourth power level is lower than the third power level.

In some embodiments, the method further involves: operating the ultrasound imaging machine in the idle mode; determining whether the ultrasound imaging machine has resumed imaging; if determined that the ultrasound imaging machine continues has not resumed imaging, changing from the idle mode to a hibernation mode that consumes power at a fifth level, wherein the fifth power level is lower than the fourth power level.

In some embodiments, the ultrasound imaging machine is communicably coupled to a multi-use electronic device for controlling the operation of the ultrasound imaging machine, and determining whether the at least one first ultrasound image generated in the first imaging mode is for viewing involves determining whether the multi-use electronic device is actively operated. In some embodiments, determining whether the multi-use electronic device is actively operated involves at least one of: measuring interaction with a user interface of the multi-use electronic device, and measuring multi-use electronic device motion.

In a second broad aspect of the present disclosure, there is provided an ultrasound imaging machine, including a processor and a memory storing instructions for execution by the processor, wherein when the instructions are executed by the processor, the ultrasound imaging machine is configured to: operate the ultrasound imaging machine in a first imaging mode to generate at least one first ultrasound image, wherein the first imaging mode consumes power at a first power level; determine whether the at least one first ultrasound image generated in the first imaging mode is for viewing; if determined that the at least one first ultrasound image generated in the first imaging mode is not for viewing, change from the first imaging mode to a second imaging mode that consumes power at a second power level, wherein the second power level is lower than the first power level; operate the ultrasound imaging machine in the second imaging mode to generate at least one second ultrasound image; determine whether the at least one second ultrasound image generated in the second imaging mode is for viewing; and if determined that the at least one second ultrasound image generated in the second imaging mode is not for viewing, change from a second imaging mode to a freeze mode that consumes power at a third level, wherein the third power level is lower than the second power level.

In some embodiments, when determining whether the at least one first ultrasound image generated in the first imaging mode is for viewing, the ultrasound imaging machine is further configured to determine if the ultrasound imaging machine has been inactive for longer than a first time period, and when determining whether the at least one second ultrasound image generated in the second imaging mode is not for viewing, the ultrasound imaging machine is further configured to determine if the ultrasound imaging machine has been inactive for longer than a second time period.

In a third broad aspect of the present embodiment, there is provided a multi-use electronic device for controlling operation of an ultrasound imaging machine, the multi-use electronic device including a processor and a memory storing instructions for execution by the processor, wherein when the instructions are executed by the processor, the multi-use electronic device is configured to: command the ultrasound imaging machine to operate in a first imaging mode, wherein the first imaging mode consumes power at a first power level; determine whether the multi-use electronic device is actively operated; and if determined that the multi-use electronic device is not actively operated, transmit information to the ultrasound imaging machine indicating that the multi-use electronic device is not actively operated; wherein based on the indication, the ultrasound imaging machine changes from the first imaging mode to a second imaging mode that consumes power at a second power level, wherein the second power level is lower than the first power level.

In some embodiments, if the multi-use electronic display device continues to not be actively operated, the multi-use electronic device is further configured to: transmit further information to the ultrasound imaging machine to indicate that the multi-use electronic device continues to not be actively operated; wherein based on the further information, the ultrasound imaging machine changes from a second imaging mode to a freeze mode that consumes power at a third level, wherein the third power level is lower than the second power level.

In some embodiments, determining whether the multi-use electronic device is actively operated involves at least one of: measuring interaction with a user interface of the multi-use electronic device, and measuring multi-use electronic device motion. In some embodiments, measuring of multi-use electronic device motion is performed by a motion sensor on the multi-use electronic device.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is an ultrasound system according to at least one embodiment of the present disclosure. Ultrasound system 100 may be operable to transmit ultrasound energy to a target object, receive ultrasound energy reflected from the target object, and generate ultrasound image data based on the reflected ultrasound energy. The ultrasound system 100 may include an ultrasound imaging machine 110 communicatively connected with a multi-use electronic device 120. In the illustrated embodiment, a wireless connection 140 may connect ultrasound imaging machine 110 with electronic device 120 to facilitate exchange of data and commands between the two.

Ultrasound imaging machine 110 may include, for example, a transducer array 102 having a number of transducer elements 104, a transmitter 108, a receiver 106, a processor 114, battery 112, and a communication (e.g., a wireless) interface 118. In some embodiments, the ultrasound imaging machine 110 may include a sensor 116

(shown in dotted outline). The ultrasound imaging machine 110 may also generally be referred to as an ultrasound machine, scanner, probe, imaging device and/or imaging apparatus herein. In some embodiments, ultrasound imaging machine 110 may be provided in the form of a handheld ultrasound probe. However, other physical forms of the ultrasound imaging machine 110 may also be possible.

Transducer elements 104 may be operable to both emit and receive ultrasound energy. When energized by a transmitter 108, the transducer elements 104 may produce a burst of ultrasound energy. The ultrasound energy produced by transducer array 102 may be directed toward a target object. Some of the ultrasound energy is reflected back to transducer array 102 as echo signals. The transducer elements 104 convert the received ultrasound energy into analog electrical signals which are then sent to receiver 106. Receiver 106 may include various well-known or future developed elements for digitizing the received ultrasound energy. The raw digitized ultrasound energy may then be transmitted to processor 114 for various processing steps. In various embodiments, transducer elements 104 can be constructed of any suitable material. For example, in some embodiments, transducer elements 104 may be formed using piezoelectric crystals. Additionally or alternatively, transducer elements 104 may be formed using capacitive micromachined ultrasonic transducers (CMUTs).

Processor 114 may be configured to apply various processing steps to the raw ultrasound data. These processing steps may be implemented in software or hardware. The processing steps may include one or more of the following: beamforming, summing, in-phase and quadrature, envelope detection and/or compression. More advanced imaging processing techniques may also be performed, including one or more of the following: spatial compounding, synthetic aperture, and multi-focus.

In various embodiments, processor 114 may also control the amount of power supplied to components and/or control their operating condition. For example, receiver 106 may be capable of operating in a normal mode and a low-power consumption mode. To reduce power consumption, processor 114 may set receiver 106 to operate in a low-power mode when receiver 106 is not required to operate.

Processed ultrasound image data may be provided to communication interface 118 for transmission to a connected device such as multi-use electronic device 120. As illustrated, a wireless connection 140 between the scanner communication interface 118 and the electronic device communication interface 128 may be formed. This connection may use any conventionally known or future developed communication protocol, such as wireless communication protocols Wi-Fi™, or Wi-Fi Direct™. In alternative embodiments, the connection between the ultrasound imaging machine 110 and the electronic device 120 may be wired. For example, the electronic device 120 may be an iOS™ device with a Lightning™ (or future iOS™) connector. In other example embodiments, the electronic device 120 may be an Android™ device with a current or future-developed Universal Serial Bus (USB) connector. A suitable wired connection may be formed between the ultrasound imaging machine 110 and an electronic device 120 using such wired connectors.

Multi-use electronic device 120 may be a smartphone, tablet computer, or other suitable device. For ease of reference, multi-use electronic device 120 may also generally be referred to as an electronic device herein. Electronic device 120 may include a display 130, input component 132, processor 124, memory 122 (as shown, storing an ultrasound app 170 for operating the ultrasound imaging machine 110), and display device communication interface 128. In some embodiments, electronic device 120 may also include sensor 136 (shown in dotted outline). Processed ultrasound image data may be received by communication interface 128 and provided to processor 124. The processed ultrasound image data may be further processed and stored in memory 122 and/or displayed on display 130. Input component 132 may receive input (e.g., via the ultrasound app 170) to control the operation of ultrasound imaging machine 110. For example, input may be received through input component 132 to request ultrasound imaging machine 110 to initiate ultrasound imaging.

In various embodiments, input component 132 may include a touchscreen, a keyboard, a mouse, a voice-activated interface or other user-machine interfaces now known or later developed.

Processor 124 on electronic device 120 may perform one or more processing steps on the processed ultrasound image data to generate an ultrasound image. For example, processor 124 may be operable to combine one or more of the frames generated from the ultrasound image data and/or perform scan conversion.

Processor 114 on ultrasound imaging machine 110 and processor 124 on electronic device 120 may also be configured to perform additional steps to determine an operating condition of ultrasound system 100. An operating condition of the ultrasound system 100 may be a state in which the ultrasound system 100 is operating. For example, an operating condition may be whether or not ultrasound images being generated are intended for viewing. In some embodiments, this determination may be made based on one or more of the raw ultrasound data, the processed ultrasound image data, and/or data from one or more of sensor 116 and/or sensor 136. As discussed below, the determined operating condition may affect a power usage level of the ultrasound imaging machine 110. In an example embodiment where the ultrasound system 100 includes an ultrasound machine 110 and a multi-use electronic device 120, the operating condition of the ultrasound system 100 as a whole may be determined based on the operating condition of the ultrasound machine 110 or the multi-use electronic device 120 individually.

In some embodiments, sensor 118 and/or sensor 136 may include a motion sensor such as an inertial measurement unit, accelerometer, a magnetometer, or a gyroscope. For example, a motion sensor on either the ultrasound imaging machine 110 and/or the electronic device 120 may be used to detect if and how each respective device is being moved. For example, absolutely no movement of ultrasound imaging machine 110 may indicate that it is resting on a stable surface and not being used to generate images for viewing. Similarly, high velocity movement of ultrasound imaging machine 110 may indicate it is being moved into place and not yet generating images for viewing.

In some embodiments, sensor 118 and/or sensor 136 may include a sensor to detect the presence of an operator. An operator sensor may include a mechanical switch, an infrared- or capacitance-based proximity sensor, and/or other conventionally known or further developed sensor for detecting the presence of a user. For example, a mechanical switch mounted on ultrasound imaging machine 110 may indicate when the user is grasping the device (e.g., with their hand).

The various components of ultrasound imaging machine 110 may be capable of operating in several different power modes, in which each of the different power modes consume power at different power levels. These different power modes may be achieved by modifying the operation of software, hardware, or some combination of both software and hardware. For example, a hardware-based power mode change may involve changing a given component from a normal operation mode to a low-power operation mode, or powering off the component completely. A software-based power mode change may involve disabling a power-intensive processing step, or reducing the number of ultrasound frames in a particular time period (e.g., reducing framerate).

Based on the operating condition of the ultrasound imaging machine 110, ultrasound imaging machine 110 may reduce power consumption by directing selected components to operate at different modes. In various embodiments, ultrasound imaging machine 110 may be configured to operate in a number of modes, each with a respective power level.

In some embodiments, ultrasound imaging machine 110 may be configured to operate in a first imaging mode which consumes power at a first level; a second imaging mode with consumes power at a second level less than the first level; and a freeze mode that consumes power at a third level less than the second level.

In various embodiments, ultrasound imaging machine 110 may implement a power management method to select amongst different power modes. Several example embodiments of the methods are described below with reference to FIG. 2 and FIG. 3.

Figure 2:
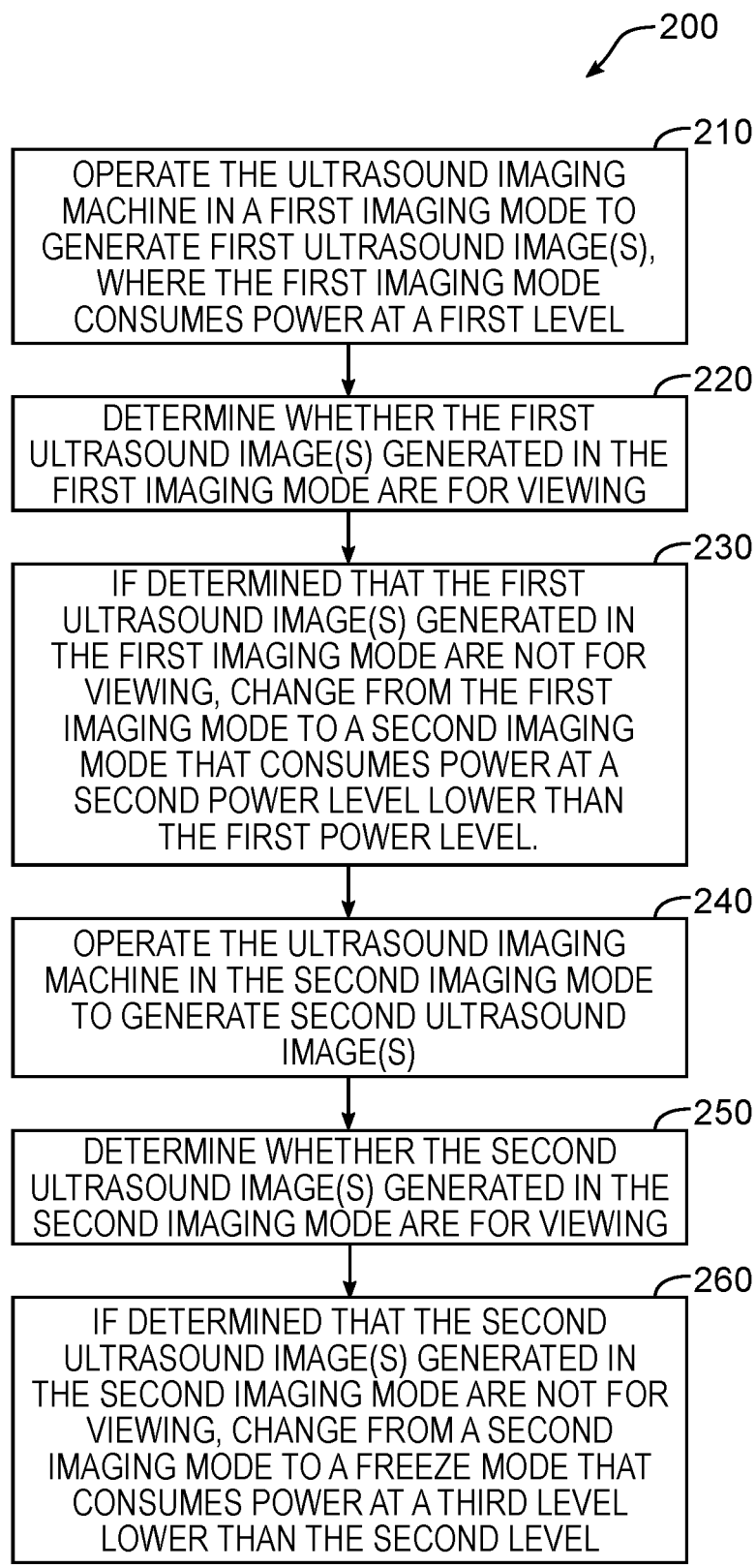
FIG. 2 shows a flowchart diagram with acts for providing power management in an ultrasound imaging machine, according to at least one embodiment of the present disclosure.

Referring to FIG. 2, shown there generally as 200 is a flowchart diagram for acts of providing power management in an ultrasound imaging machine, according to at least one embodiment of the present disclosure.

At 210, the ultrasound imaging machine 110 may be operated in a first imaging mode to generate at least one first ultrasound image. Ultrasound images may be generated by transmitting ultrasound pulses and processing the received ultrasound echoes. While operating in the first imaging mode, ultrasound imaging machine 110 may consume power at a first level. In some embodiments, during this first imaging mode, various power-intensive imaging parameters or features (e.g., higher frame rate, spatial compounding, multi-line acquisition) may be enabled so that optimal images are acquired.

At 220, ultrasound imaging machine 110 may determine whether the at least one first ultrasound image generated while operating in the first imaging mode is for viewing. For example, determining whether the at least one first ultrasound image is for viewing may be based on one or more of: analyzing the at least one first ultrasound image, determining if ultrasound imaging machine 110 is being actively operated and/or determining if electronic device 120 is being actively operated. In various embodiments, determining if ultrasound imaging machine 110 and/or electronic device 120 is being actively operated may be based on sensor data detected by a sensor (e.g., either sensor 116 on ultrasound imaging machine 110 and/or sensor 136 on electronic device 120, examples of which were discussed above).

In some embodiments, determining whether the at least one first ultrasound image is for viewing may be based on analysis of the at least one first ultrasound image. The image analysis may be used to infer how the ultrasound imaging machine 110 is moving or what type of material is being imaged. For example, ultrasound imaging machine 110 may determine if the ultrasound imaging machine 110 is imaging air or imaging tissue. Due to the difference in impedance between the transducer and air, and scattering, very little of the ultrasound energy may be reflected back to the transducer if the transducer is imaging air. The received echoes will have a substantially lower amplitude and this may result in dark pixels. As a result, measuring the amount of received echoes with low amplitude or number of dark pixels in an image generated from the received ultrasound echo data may be used to determine if the ultrasound machine 110 is imaging air. If it is determined that the machine 110 is imaging air, the machine 110 may infer that the machine is not in contact with tissue and that the generated images are not for viewing. In another example, ultrasound imaging machine 110 may determine how the ultrasound imaging machine 110 is moving by analyzing two or more first ultrasound images.

Additionally or alternatively, determining whether the at least one first ultrasound image is for viewing may be based on whether the ultrasound imaging machine 110 is being actively operated. For example, if ultrasound imaging machine 110 has been inactive for a longer than a first time period, this may indicate that the ultrasound images being generated are not for viewing. Various methods may be used to determine if ultrasound imaging machine 110 is being actively operated, including measuring motion and/or measuring user interaction. During typical imaging intended for viewing, some movement of the ultrasound machine 110 is expected. As a result, absolutely no motion may indicate that the ultrasound machine 110 is inactive (e.g. resting on a stable surface) and is not being used to generate images for viewing. Similarly, excessive motion may indicate that ultrasound imaging machine 110 is being moved into place or transported, and the images generated are not for viewing.

In various embodiments, a motion sensor may include an accelerometer, a magnetometer, and/or a gyroscope, or any other conventionally known or future developed motion sensor. Additionally or alternatively, various technologies for position tracking may be used for motion sensing, such as active or passive retroreflective optical markers, image or video tracking, mechanical linkage, and/or magnetic based tracking systems. One or more of position, velocity, acceleration, orientation, angular velocity and angular acceleration may be used to determine the operating condition of the ultrasound imaging machine 110 (e.g., to infer whether the generated images are for viewing). For example, instantaneous and/or interval-based measurements may be used. In various embodiments, measurements from one or more sensors (e.g., sensor 116 discussed above) may be used. In various embodiments, measurements may be classified to determine whether they match predetermined movement patterns associated with generating images for viewing.

Determining whether the at least one first ultrasound image is for viewing may also be alternatively or additionally determined based on the operating condition of electronic device 120, including whether it is actively operated. Various methods may be used to determine if electronic device 120 is being actively operated. For example, these methods may include measuring interaction with the input components (e.g., input component 132 shown in FIG. 1) and/or measuring the motion of the electronic device 120. Measuring user interaction with the input components may include measuring interactions with a touchscreen, measuring sound levels with a microphone, and/or using a camera/depth sensor to detect presence or absence of an ultrasound operator. For example, a camera may be used to detect the presence of a user's face. Alternatively or additionally, motion sensors within electronic device 120 may be used to infer whether the electronic device 120 is being actively used based on the position, movement, and/or orientation of the electronic device 120.

In some embodiments, two or more methods may be used to determine whether the ultrasound imaging machine 110 and/or electronic device 120 is actively operated. For example, measurements from a motion sensor may be combined with image analysis. In another example, selected parameters such as an imaging pre-set may be used to classify motion sensor measurements as actively imaging or not (e.g., certain ultrasound imaging machine non-movement may indicate an absence of operator activity for a type of imaging pre-set, but the same non-movement may be normal imaging activity for another type of imaging pre-set).

In some embodiments, it may be desirable to explicitly disable determining whether the ultrasound imaging machine 110 and/or electronic device 120 is actively operated based on motion sensing. The ability to disable whether the motion sensor is used to determine active operation may be configured by the user and/or based on an imaging pre-set. For example, it may be desirable to disable motion sensor-based active operation determination when the ultrasound imaging machine 100 is used in a monitoring application and is expected to remain stationary for long periods of time.

Returning to FIG. 2, at 230, if it is determined that the at least one first ultrasound image generated is not for viewing at 220, the ultrasound imaging machine 110 may change from the first imaging mode to a second imaging mode that consumes power at a second power level that is lower than the first power level.

A variety of techniques may be used to reduce power consumption between the first imaging mode and the second imaging mode. For example, switching from this first imaging mode to the second imaging mode may involve modifying or disabling various power-intensive imaging parameters and/or features used during the first imaging mode for obtaining images of the highest quality. Since it is determined from the operating condition of the ultrasound imaging machine 110 and/or electronic device 120 that the generated ultrasound images are not for viewing, these parameters and/or features may be modified or disabled without consequence to the user's perception of imaged tissue. For example, some of the actions that may be taken at act 230 may include reducing frame rate, reducing transmit pulse amplitude, and/or disabling advanced image processing.

The frame rate of ultrasound imaging may depend on the amount of time between successive image frames. Reducing the frame rate may reduce power consumption by reducing how frequently energy is required to generate an ultrasound pulse, digitize the received echoes, and process the received echoes into ultrasound image data. In various embodiments, the frame rate may be a software-controlled parameter. A typical ultrasound frame rate may be 30 frames per second. The frame rate can determine the temporal resolution of the image: faster frame rates may lead to smoother sequences, and lower frame rates may cause noticeable and undesirable jitter in the image. Since ultrasound imaging machine 110 is not actively imaging in the second imaging mode, the lower visual quality of the lower frame rates may not be noticeable, and thus, power can be saved while imaging in this second mode.

Power consumption may also be reduced by reducing the amplitude of the transmitted pulse. Reducing the amplitude may be accomplished by reducing the voltage supplied to the transmitter, for example. A reduced-amplitude ultrasound pulse may require less energy, and result in a weaker ultrasound beam that is not able to penetrate as deeply. Similar to the result of using a lower frame rate, the visual effect of a weaker ultrasound beam that does not penetrate as deeply may not be readily be noticed when imaging in the second mode because the ultrasound imaging machine 110 is not generating images for viewing. Nevertheless, power savings can be achieved.

Power consumption may also be reduced by disabling advanced image processing modes. Any currently known or future developed advanced image processing techniques could be disabled, including spatial compounding, synthetic aperture, and multi-focus. Power consumption may be reduced as a result of generating an image with fewer transmit and receive events. For example, a spatially-compounded image frame may be based on three or more individual frames, each consisting of multiple transmit and receive events. Disabling spatial compounding may thus reduce the number of transmit and receive events required to acquire at least some of these frames (and thus power consumed).

It may be desirable to disable certain advanced imaging processing techniques based on the determination at act 220. For example, if it is determined that ultrasound images being generated at act 220 are not for viewing because the ultrasound imaging machine 110 is being subjected to large amounts of movement, disabling advanced image processing techniques may allow for reduced overall power consumption. This may be because such advanced image processing techniques assume the ultrasound imaging machine 110 is generally not being moved between multiple data acquisition events, so large amounts of ultrasound machine 110 movement may make it unnecessary for the advanced imaging processing techniques to be enabled. For example, spatial compounding, synthetic aperture, and multi-focus rely on combining data from a large number of transmissions and will not produce quality images if the ultrasound imaging machine is moving between transmissions.

In some embodiments, changing from the first imaging mode to the second imaging mode may involve modifying the instructions for execution by the processor. For example, ultrasound machine 110 may include programmable logic such as a field programmable gate array (FPGA) that can change from a first configuration (e.g., first bitstream) to a second configuration (e.g., second bitstream). The FPGA may consume less power while operating in the second configuration as opposed to the first configuration (e.g., because the second configuration has fewer instructions than the first configuration, and the second configuration may thus configure the FPGA to power fewer of the available gates available on the FPGA). For example, a first configuration may include advanced imaging processing techniques like spatial compounding, synthetic aperture, and/or multi-focus that, due to their more complex nature, require more instructions and gates to be powered, while the second configuration may only include basic B-Mode processing which requires fewer instructions and thus fewer gates to be powered. To resume operating in the first imaging mode, the FPGA can be quickly re-programmed with the first configuration.

At 240, the ultrasound imaging machine 110 may be operated in a second imaging mode to generate at least one second ultrasound image. While operating in the second imaging mode, ultrasound imaging machine 110 may consume power at a second level lower than the first level. In a manner similar to act 220, the at least one second ultrasound image may be generated by transmitting ultrasound pulses and processing the received ultrasound echoes.

At 250, ultrasound imaging machine 110 may determine whether the at least one second ultrasound image generated while operating in the second imaging mode is for viewing. In some embodiments, determining whether the at least one second ultrasound image is for viewing may be performed in a manner similar to determining whether the at least one first ultrasound image is for viewing in act 220.

For example, in some embodiments, determining whether the at least one second ultrasound image is for viewing may be based on determining if the ultrasound imaging machine 110 has been inactive or not actively imaging for a period longer than a second time period. In various embodiments, the second time period may be measured with respect to either when the machine 110 first determines that it is not actively operated, or from when the machine 110 changed to the second imaging mode.

At 260, if it is determined that the at least one second ultrasound image generated is not for viewing at 250, the ultrasound imaging machine 110 may change from the second imaging mode to a freeze mode that consumes power at a third power level that is lower than the second power level.

In various embodiments, additional operating modes with corresponding respective power levels may be included. For example, ultrasound imaging machine 110 may be configured to operate in an idle mode, where the idle mode consumes less power than the freeze mode. Ultrasound system 100 may change from freeze mode to idle mode based on whether the ultrasound imaging machine 100 or the display device 120 or both are actively operated.

In various embodiments, ultrasound imaging machine 110 may also be configured to operate in a hibernation mode, where the hibernation mode consumes less power than the idle mode. Ultrasound system 100 may change from hibernation mode to idle mode based on whether the ultrasound imaging machine 100 or the display device 120 or both are actively operated.

Figure 3:
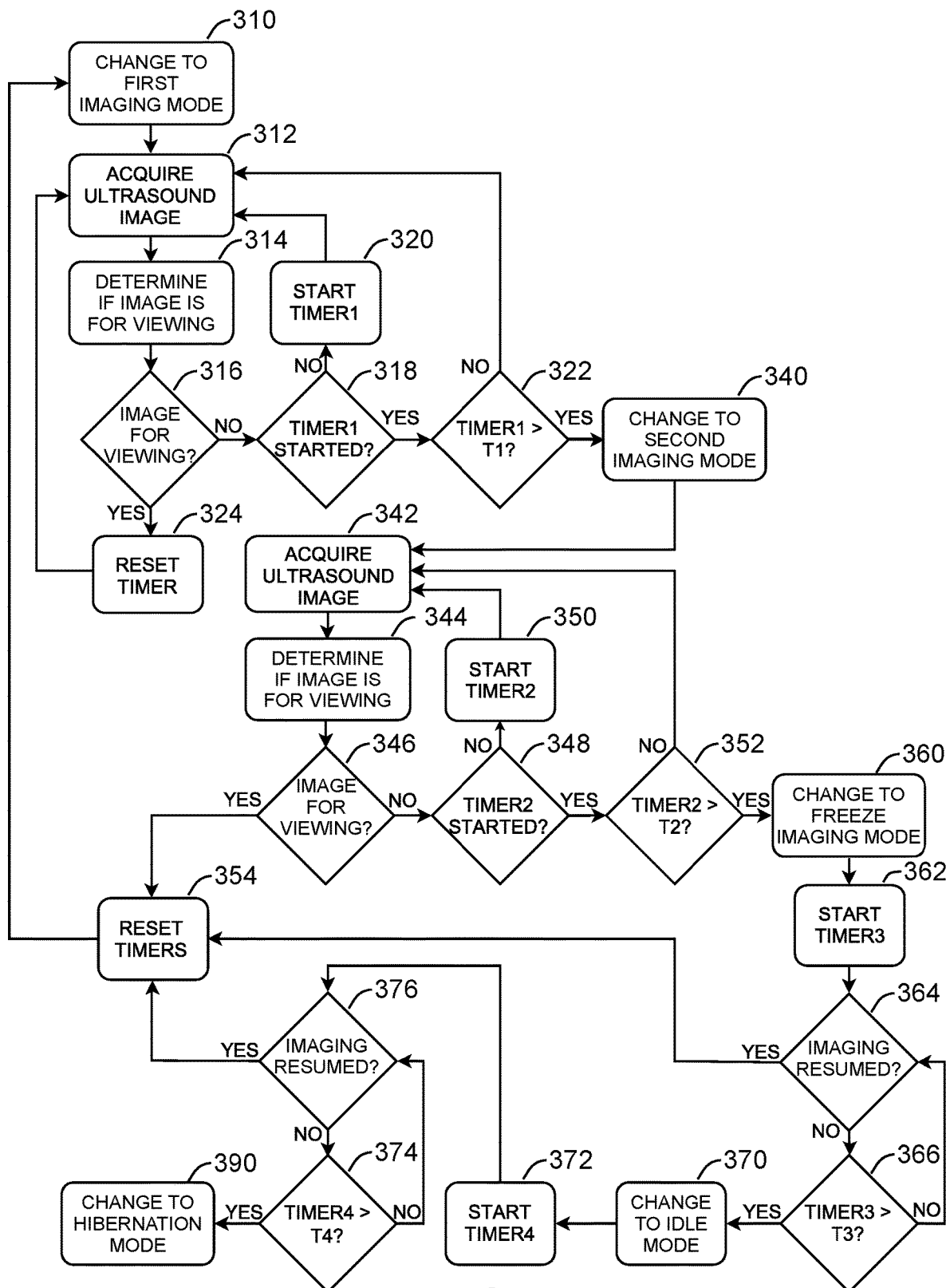
FIG. 3 shows a flowchart diagram with acts for providing power management in an ultrasound imaging machine, according to at least another embodiment of the present disclosure.

Referring to FIG. 3, shown there generally as 300 is a flowchart diagram of acts for providing power management in an ultrasound imaging machine, according to at least one embodiment of the present disclosure. As discussed below, some acts shown in FIG. 3 can be analogous to corresponding acts shown in FIG. 2. In various embodiments, the method of FIG. 3 may be performed by the ultrasound imaging machine 110 shown in FIG. 1.

At 310, the ultrasound imaging machine 110 may be placed into a first imaging mode that consumes power at a first level. This first imaging mode may be the mode for actively generating high-quality ultrasound images of tissue. For example, an ultrasound imaging machine 110 may be placed into this mode when an imaging pre-set is first selected, or upon receipt of an 'unfreeze' command for the ultrasound machine 110 to begin active ultrasound imaging.

At 312, ultrasound imaging machine 110 may acquire an ultrasound image. As discussed above, the image acquisition may involve one or more transmit and receive events and various associated processing steps.

At 314, ultrasound imaging machine 110 may determine if the generated ultrasound image is for viewing. Determining whether the generated ultrasound image is for viewing may be may be determined in a manner substantially similar to act 220 with respect to FIG. 2. For example, determining whether the generated ultrasound image is for viewing may include analyzing the ultrasound image. Additionally or alternatively, determining whether the generated ultrasound image is for viewing may also involve determining whether ultrasound imaging machine 110 or electronic device 120 or both are being actively operated.

If, at 316, the ultrasound imaging machine 110 determines that the generated ultrasound image if not for viewing, ultrasound imaging machine 110 may proceed to act 318. If, at 316, the ultrasound imaging machine 110 determines that the generated ultrasound image is for viewing, ultrasound imaging machine 110 may proceed to act 324. At act 324, a first time (shown as 'Timer 1' in act 318) may be reset. Ultrasound imaging machine 110 may then return to act 312 to continue ultrasound image acquisition. During typical live scanning or continuous active imaging, ultrasound imaging machine 110 may cycle through acts 312, 314, 316, and 324.

If the result of act 316 is that the generated ultrasound images are not for viewing, at 318, the ultrasound imaging machine 110 may determine if the first timer (referred to herein also as 'Timer 1') has been started. If 'Timer 1' has not been started 'Timer 1' may be started (act 320). Ultrasound imaging machine 110 may then return to act 312 to continue ultrasound image acquisition. If, at 318, ultrasound imaging machine 110 determines that 'Timer 1' has already been started, ultrasound imaging machine 110 may proceed to act 322.

At 322, ultrasound imaging machine 110 may determine if the time elapsed on 'Timer 1' exceeds a first time period (shown as 'T1' in FIG. 3). If the time elapsed from the start of 'Timer 1' is less than the first time period (e.g., the time elapsed does not exceed the first time period 'T1'—the 'NO' branch at act 322), ultrasound imaging machine 110 may return to act 312 to continue ultrasound image acquisition. So long as it is determined that generated ultrasound images are not for viewing at act 316, acts 312, 314, 316, 318, and 322 may be repeated until the time elapsed for 'Timer 1' exceeds the first time period 'T1'.

If, at 322, the time elapsed on 'Timer 1' exceeds the first time period 'T1', an action to reduce the power consumption of the ultrasound machine 110 may be performed, and the ultrasound machine 110 may proceed to act 340.

At 340, ultrasound machine 110 may be changed to operate in a second imaging mode, where the ultrasound machine 110 consumes power at a second level which is lower than the first level. This act may be performed when the ultrasound imaging machine 110 and/or the electronic device 120 is determined to be inactive or not actively imaging for a period of time exceeding a first time period 'T1'. For example, if the ultrasound imaging machine 110 was set down on a table, the ultrasound imaging machine 110 may automatically change to a second, lower-power imaging mode after a specified delay.

In the second imaging mode, some of the acts 342 to 360 are performed in manner similar to the way acts 312-340 in the first imaging mode are performed.

At 342, an ultrasound image is acquired in a similar manner to act 312, except power is consumed at a second level that is lower than the first level. The reduction in power consumption may be due to one or more of reduced frame rate, reduced transmit amplitude, or disabled advanced image processing steps.

In some embodiments, changing to the second imaging mode may involve reducing the bit resolution of the analog to digital converters. For example, the bit resolution may be 16 bit in the first imaging mode and 14 bit in the second imaging mode.

While operating in the second imaging mode at a second power level, if it is determined that generated ultrasound images are intended for viewing at act 346, the ultrasound imaging machine 110 may reset the timers in act 354 and proceed to revert to the first imaging mode at act 310. For example, an ultrasound imaging machine 110 may have been temporarily placed on a table and had changed to the second, lower-power imaging mode at act 340. However, act 344, it may be determined that an ultrasound image generated is again intended for viewing (e.g., it may be sensed via a sensor 116 that the ultrasound machine 110 has moved). This may result in the flow chart proceeding to the 'YES' branch of act 346, and the resetting of timers at act 354 to resume the first imaging mode. Generally, this may allow the ultrasound machine 110 to quickly resume the first, higher-power imaging mode when the ultrasound machine 110 is picked up in the second imaging mode and place against a patient.

At 354, the timers are reset. This act is performed after act 346, act 364, or act 376 in response to an indication that ultrasound system 100 should return to the first imaging mode in act 310.

Acts 348, 350, and 352 are performed in as manner similar to the way act 318, 320, and 322 are performed, except a second timer 'Timer 2' is used instead of 'Timer 1', and the amount of time elapsed by 'Timer 2' is compared to a second time period 'T2'. As discussed above, in various embodiments, the second time period may be measured with respect to different beginning points in time (e.g., either when the machine 110 first determines that it is not actively operated, or from when the machine 110 changed to the second imaging mode). However, in the example embodiment of FIG. 3, the second time period is independent of the first time period, and begins at act 350.

At 360, ultrasound imaging machine 110 may be changed to operate in a freeze mode, where ultrasound imaging machine 110 consumes power at a third level that is lower than the second level. Freeze mode may involve the cessation of image generation. Operating in freeze mode may also involve turning off components or changing them to operate in a low power or sleep mode. For example, the analog to digital converters may be directed to operate in a sleep mode or powered down completely to conserve power.

Since the ultrasound imaging machine 110 may no longer be acquiring ultrasound data and generating ultrasound images, different criteria may be used to determine whether to initiate further power-reduction actions. Acts 362-390 show additional optional acts to further power down an ultrasound imaging machine 110. These further lower-level power modes are not required and may not be present in some embodiments.

For example, in the example embodiment of FIG. 3, at 362, a third timer 'Timer 3' may be started. 'Timer 3' may be used to keep track of how long ultrasound imaging machine 110 has been operating in freeze mode.

At 364, ultrasound imaging machine 110 may determine if user input has requested that imaging be resumed. If the user has requested to restart/resume imaging, the timers are reset at act 354 and the operating mode is changed to the normal imaging mode in act 310. The determination made at act 364 may be made in various ways. For example, in some embodiments, the determination may be made using some of the mechanisms discussed above that do not require the generation of ultrasound images. For example, some such mechanism include reading input from a motion sensor to detect movement of the ultrasound machine 110, so as to automatically resume active imaging. Additionally or alternatively, the resumption of imaging may be determined based on user input (e.g., from the electronic device 120) that indicates an 'unfreeze' command.

If restarting imaging has not been requested, the ultrasound machine 110 may proceed to act 366. At 366, the ultrasound imaging machine 110 may determine whether the time elapsed on 'Timer 3' has exceeded a third time period 'T3'. If at 366, 'Timer 3' has exceeded the third time period 'T3', the operating mode may be further changed to an idle mode at act 370. If 'Timer 3' has not exceeded the third time period 'T3', the machine may return to act 364 to determine if imaging has been resumed. As with the second time period, in various embodiments, the third time period may be measured with respect to different beginning points in time (e.g., either when the machine 110 first determines that it is not actively operated, or from when the machine 110 changed to the second imaging mode, or from when the machine 110 changed to the third imaging mode). In the example embodiment of FIG. 3, the third time period is independent of either the first time period or the second time period, and is started at act 362.

At 370, ultrasound imaging machine 110 changes from the freeze mode to idle mode. Idle mode may consume power at fourth level that is lower than the third level. Changing to idle mode may also involve turning off additional components or changing individual components to operate in a low power or idle mode.

For example. in some embodiments, the ultrasound machine 110 may include programmable logic such as a field programmable gate array (FGPA) and changing to idle mode may involve deprogramming the FPGA or resetting the FPGA to an un-programmed state. The FPGA may consume less power in an un-programmed state than in a programmed state (e.g., due to fewer gates being powered). If imaging is to be resumed, the FPGA can be re-programmed on the fly.

In some embodiments, changing to idle mode may also involve disabling power to power rails, and/or lowering CPU frequency.

At 372, a fourth timer 'Timer 4' can be started. 'Timer 4' may be used to keep track of how long ultrasound imaging machine 110 has been operating in idle mode. Similar to the determination made at act 364, the determination made at act 376 may be made in various ways. For example, in some embodiments, the determination may be made based on input from a motion sensor. Additionally or alternatively, the determination may be made via the receipt of user input (e.g., from an electronic device 120 that is communicating with the ultrasound machine 110).

If imaging has not been resumed or restarted by the time 'Timer 4' reaches the expiry of the fourth time period 'T4' as determined in act 374, the method may proceed to act 390.

At 390, the ultrasound imaging machine 110 changes from idle mode to hibernation mode. Hibernation mode may consume power at a fifth level, where the fifth level is lower than the fourth level. Activation of hibernation may involve turning off further components or changing them to operate in a low power or idle mode.

In some embodiments, changing to hibernation mode may include disabling part or all of the communication interface 118. Communication interface may use two or more communication protocols and changing to hibernation mode may involve turning off one or more of the protocols. For example, communication interface 118 may include both Wi-Fi™ and Bluetooth™ communication protocols, and changing to hibernation mode may involve disabling power intensive Wi-Fi™ radios and relying on Bluetooth™.

In some embodiments, there is no hibernation mode, and ultrasound imaging machine 110 is completely shutdown at act 390.

In some embodiments, the time periods may be user configurable. For example, one or more of the first time period ('T1'), second time period ('T2'), third time period ('T3'), and fourth time period ('4') may be configured by the user through input component 132 of electronic device 120 (as shown in FIG. 1).

Figure 4:
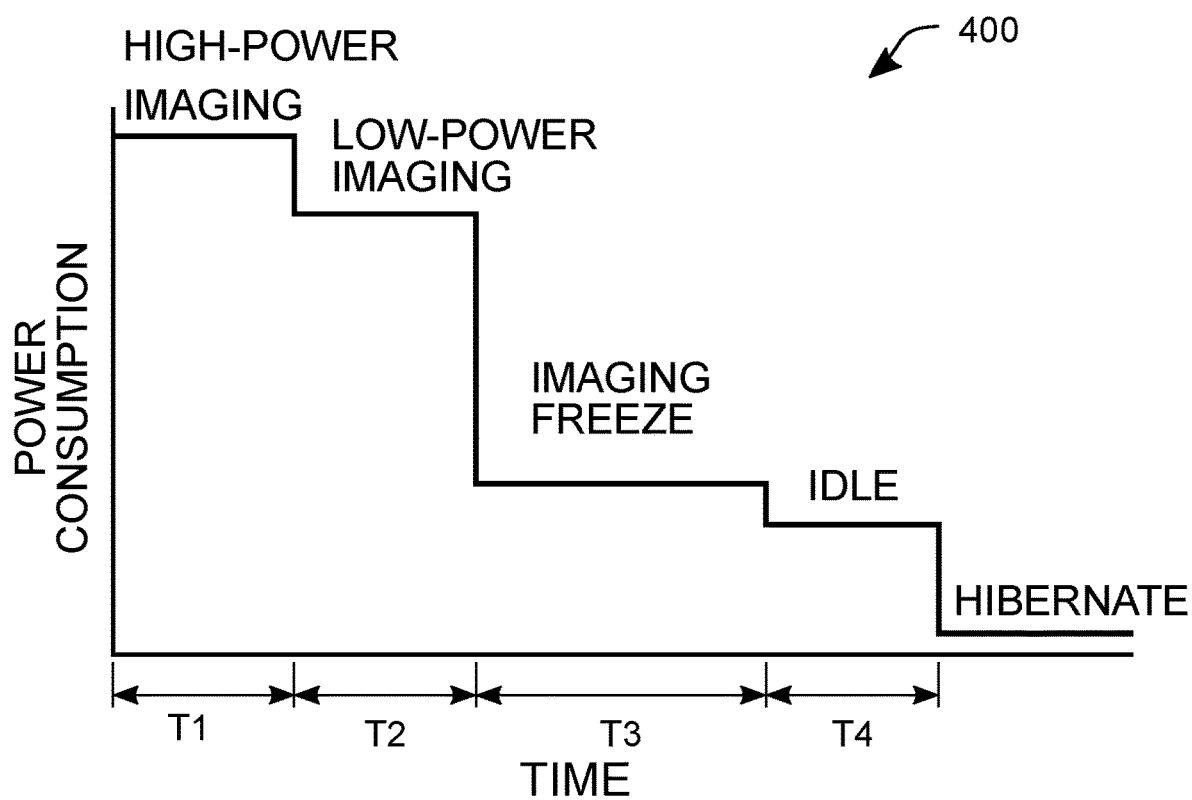
FIG. 4 shows a plot of power consumption over time, according to at least one embodiment of the present disclosure.

Referring to FIG. 4, shown there generally as 400 is a plot of power consumption over time, according to at least one embodiment of the present disclosure. This embodiment is an ultrasound imaging machine 110 (as shown in FIG. 1) that is configured to operate at five (5) power modes: high-power imaging mode, low-power imaging mode, freeze mode, idle mode, and hibernation mode. In this embodiment, the high-power mode may be considered analogous to the first imaging mode, and the low-power imaging mode may be considered analogous to the second imaging mode discussed herein. In discussing FIG. 4, reference may also be made to elements shown in FIG. 1, and the method of FIG. 3.

The plot of FIG. 4 shows the power consumption of an ultrasound imaging machine 110 as a function of time when it is generating images that are not for viewing (e.g., in the high-power and low-power imaging modes) and then when it is no longer actively imaging (e.g., in the imaging freeze, idle, and hibernate modes), in an example embodiment. For example, FIG. 4 may show the progression of power consumed during operation in different imaging modes as the method of FIG. 3 is executed to progressively reduce power consumption.

Referring simultaneously to FIGS. 4 and 3, an ultrasound imaging machine 110 may change from the high-power imaging mode to the low-power imaging mode after a time period of 'T1' has elapsed while the images generated by the ultrasound imaging machine 110 are determined to be not for viewing. As discussed above, whether a generated image is for viewing may be determined based on various factors. For example, these factors may include at least one of: image analysis of the generated ultrasound image, active operation of the ultrasound machine 110, and/or active operation of the electronic device 120. As shown in FIG. 4, the power consumption of the ultrasound imaging machine 110 may decrease from a first level to a second level when switching from a high-power imaging mode to a low-power imaging mode.

Once a second time period 'T2' has elapsed while the ultrasound imaging machine 110 is in the low-power imaging mode and the generated ultrasound images are continued to be determined to be not for viewing, the ultrasound machine 110 may change to a freeze mode. The ultrasound machine 110 may consume less power while operating in the freeze mode than when the machine 110 is operating in the first imaging mode and the second imaging mode.

While operating in freeze mode, active ultrasound image acquisition may be stopped. This may result in the ultrasound machine 110 ceasing to transmit and receive ultrasound pulses, so as to reduce the power consumed. In addition to reducing power consumption, stopping imaging when the ultrasound machine 110 is not being used intentionally may offer additional benefits such as reducing wear on components and preventing patients from being inadvertently exposed to ultrasound energy. While ultrasound energy is generally considered safe, patient exposure is still recommended to be as low as reasonable achievable (e.g., the ALARA principle).

Switching to a low-power imaging mode from the high-power imaging mode may allow the ultrasound machine 110 to quickly return to the high-power imaging mode. For example, some traditional power-saving techniques may automatically switch from a regular imaging mode to a freeze mode prematurely. This may cause inconvenience for a user as they may have to manually enter an 'unfreeze' command to resume imaging when they were expecting the ultrasound machine 110 to still be actively imaging. To avoid this, some other traditional power-saving techniques may enter a low-power imaging mode indefinitely. However, such implementations may unnecessarily drain power if there is no intention to resume generation of images for viewing.

By using the tiered, progressive approach that changes the ultrasound machine 110 first from a high-power imaging mode to a low-power imaging mode, and then subsequently from the low-power imaging mode to a freeze mode, the present embodiments may balance these interests. For example, power may still be conserved in the low-power imaging mode while still allowing high-quality imaging to be resumed without user input being required.

Referring back to FIG. 4, after a third time period (T3) has elapsed with the ultrasound machine 110 in freeze mode, the machine 110 may change to an idle mode. The idle mode may consume power at a fourth level that is lower than the third level while operating in freeze mode.

As noted above, while operating in the idle mode, the ultrasound machine 110 may be returned to the first imaging mode by various mechanisms, such as a user input. For example, having user input return the ultrasound machine 110 may prevent unexpected generation of ultrasound energy, which may be desirable for adhering to the ALARA principle.

After a fourth time period 'T4' has elapsed with the ultrasound imaging machine 110 in idle mode, the ultrasound machine 110 may change to a hibernate mode. The hibernate mode may consume power at a fifth level lower than the fourth level of the idle mode.

While in hibernate mode, ultrasound imaging machine 110 may further reduce power consumption by powering down components in a manner that may require a longer period to re-start and start imaging. However, by providing a tiered approach to power consumption, the present embodiments balance the user inconvenience of being able to restart imaging quickly with conserving battery power.

FIG. 4 has been illustrated without specific numeric values on the Y-axis. However, in some example embodiments, the ultrasound machine 110 may consume approximately 15 watts (W) in the high-power imaging mode, 13 W in low-power imaging mode, 5 W in freeze mode, 4 W in idle mode and less than 100 milliwatts (mW) in hibernation mode. The relative power consumption levels during each imaging mode is shown for illustration purposes only; other relative power consumption levels may be possible in different embodiments.

Figure 5:
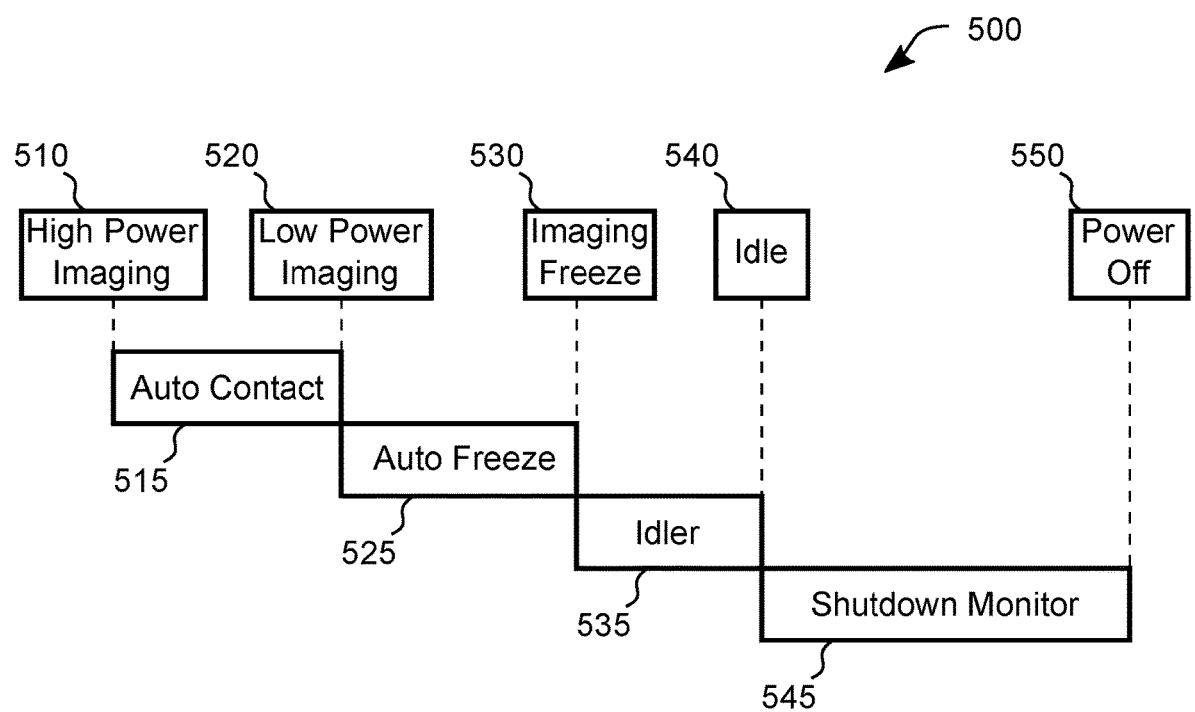
FIG. 5 shows a state diagram of an ultrasound imaging machine, according to at least one embodiment of the present disclosure.

Referring to FIG. 5, shown there generally as 500 is a state diagram of an ultrasound imaging machine, in accordance with at least one embodiment of the present disclosure. FIG. 5 illustrates the tiered, progressive reduction in power consumption across multiple imaging modes in another embodiment. In discussing FIG. 5, reference may also be made to the elements of FIG. 1.

In the embodiment of FIG. 5, an ultrasound machine 110 may be operating in a first imaging mode 510 when it is set down by an operator. An auto contact process 515 may determine whether the ultrasound machine is generating images for viewing. If the auto contact process (e.g., through image analysis) determines that images being generated are not for viewing, the ultrasound machine 110 may transition the ultrasound machine 110 to a second, lower-power imaging mode 520. While in the second imaging mode, an auto freeze process 525 may determine if the ultrasound machine 110 continues to generate images for viewing. If the auto freeze process (e.g., through lack of input indicating motion from a motion sensor) determines that the ultrasound machine 110 continues to generate images not for viewing, the ultrasound machine 110 may be changed to a freeze mode 530. Further, an idler process 535 may change the ultrasound machine 110 to an idle mode 540 after a certain amount of time has elapsed, and shutdown monitor 545 may change the ultrasound machine 110 to a power off state 550 after another amount of time has elapsed.

Figure 6:
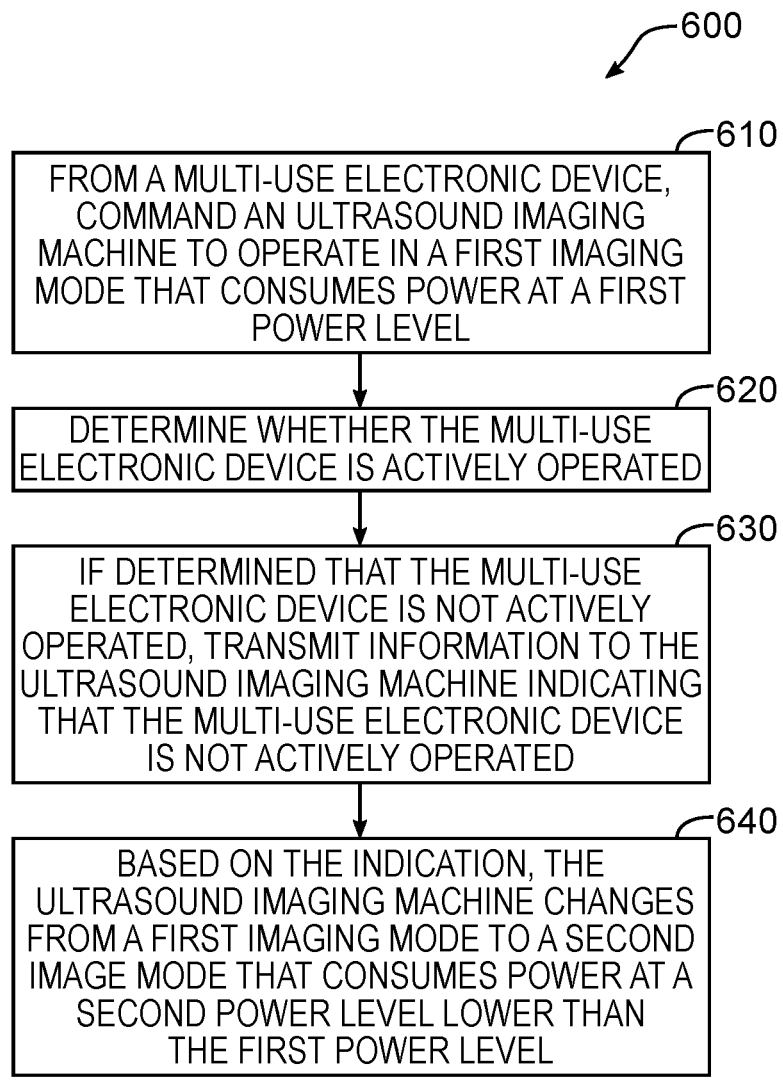
FIG. 6 shows a flowchart diagram with acts by a multi-use electronic device to control power management in an ultrasound imaging machine, according to at least one embodiment of the present disclosure.

Referring to FIG. 6, shown there generally as 600 is a flowchart diagram with acts by a multi-use electronic device to control power management in an ultrasound imaging machine, according to at least one embodiment of the present disclosure. The multi-use electronic device 120 (as shown in FIG. 1) may include a processor and a memory storing instructions for execution by the processor. When the instructions are executed by the processor, the multi-use electronic device 120 may be configured for controlling operation of the ultrasound imaging machine 110. In discussing the method of FIG. 6, reference may also be made to the At 610, the multi-use electronic device 120 may command ultrasound imaging machine 110 to operate in a first imaging mode where the first imaging mode consumes power at a first power level.

At 620, the multi-use electronic device 120 may determine whether the multi-use electronic device is actively operated. In various embodiments, determining whether electronic device 120 is actively operated may be based on various factors. For example, one or more of: measuring interaction with a user interface of the electronic device 120, and measuring motion of the electronic device 120 may be used to determine whether the electronic device 120 is being actively operated. As discussed above with reference to act 220 in FIG. 2, determining whether electronic device 120 is actively operated may be based on sensor data detected by a sensor (e.g., sensor 136 on electronic device 120).

A variety of techniques may be used to measure interaction with a user interface of the electronic device 120. In various embodiments, measuring user interface interaction may include one or more of the following: measuring contact with a touchscreen of the electronic device 120, using face detection mechanisms available on the electronic device 120, measuring sound with a microphone, and any other known or future developed user interaction quantification method.

Motion of the electronic device 120 may be measured with one or more sensors. As discussed herein, sensor 136 may include a motion sensor such as an inertial measurement unit, accelerometer, a magnetometer, or a gyroscope. Sensor 136 may be used to quantify one or more of: position, velocity, acceleration, orientation, angular velocity, and angular acceleration.

At 630, if it is determined that the multi-use electronic device 120 is not actively operated, the multi-use electronic device 120 may transmit information to the ultrasound imaging machine 110 indicating that the multi-use electronic device 120 is not actively operated.

Additionally or alternatively, electronic device 120 may periodically transmit information to the ultrasound imaging machine 110 indicating that the electronic device 120 is actively operated, and the absence of this transmission may be used to indicate that the electronic device is not actively operated.

At 640, based on the indication that the electronic device 120 is not actively operated, the ultrasound imaging machine 110 may change from the first imaging mode to a second imaging mode that consumes power at a second power level where the second power level is lower than the first power level.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of managing power consumption in an ultrasound imaging machine, the method comprising:
   operating the ultrasound imaging machine in a first imaging mode to generate at least one first ultrasound image, wherein the first imaging mode consumes power at a first power level;
   determining whether the at least one first ultrasound image generated in the first imaging mode is for viewing;
   if determined that the at least one first ultrasound image generated in the first imaging mode is not for viewing, changing from the first imaging mode to a second imaging mode that consumes power at a second power level, wherein the second power level is lower than the first power level;
   operating the ultrasound imaging machine in the second imaging mode to generate at least one second ultrasound image;
   determining whether the at least one second ultrasound image generated in the second imaging mode is for viewing; and
   if determined that the at least one second ultrasound image generated in the second imaging mode is not for viewing, changing from a second imaging mode to a freeze mode that consumes power at a third level, wherein the third power level is lower than the second power level.

2. The method of claim 1, wherein the determining whether the at least one first ultrasound image generated in the first imaging mode is for viewing comprises determining if the ultrasound imaging machine has been inactive for longer than a first time period, and wherein the determining whether the at least one second ultrasound image generated in the second imaging mode is for viewing comprises determining if the ultrasound imaging machine has been inactive for longer than a second time period.

3. The method of claim 2, wherein at least one of the first time period and the second time period is user configurable.

4. The method of claim 1, wherein a frame rate of imaging comprises the time between a first transmit sequence and a second transmit sequence, and wherein the changing from the first imaging mode to the second imaging mode comprises reducing the flame rate of imaging.

5. The method of claim 1, wherein the changing from the first imaging mode to the second imaging mode comprises reducing a transmit amplitude of ultrasound pulses transmitted from the ultrasound imaging machine.

6. The method of claim 1, wherein the determining whether the at least one first ultrasound image generated in the first imaging mode is for viewing comprises analyzing the at least one first ultrasound image.

7. The method of claim 1, wherein the determining whether the at least one first ultrasound image generated in the first imaging mode is for viewing comprises reading a motion sensor.

8. The method of claim 7, wherein the motion sensor comprises at least one of an accelerometer, a magnetometer, and a gyroscope.

9. The method of claim 1, wherein changing from the first imaging mode to the second imaging mode comprises disabling an advanced imaging processing mode.

10. The method of claim 9, wherein the advanced imaging processing mode comprises at least one of: spatial compounding, synthetic aperture, and dual focus.

11. The method of claim 1, wherein the method further comprises:
   operating the ultrasound imaging machine in the freeze mode;
   determining whether the ultrasound imaging machine has resumed imaging; and
   if determined that the ultrasound imaging machine has not resumed imaging, changing from a freeze mode to an idle mode that consumes power at a fourth power level, wherein the fourth power level is lower than the third power level.

12. The method of claim 11, wherein the method further comprises:
   operating the ultrasound imaging machine in the idle mode;
   determining whether the ultrasound imaging machine has resumed imaging;
   if determined that the ultrasound imaging machine has not resumed imaging, changing from the idle mode to a hibernation mode that consumes power at a fifth level, wherein the fifth power level is lower than the fourth power level.

13. The method of claim 1, wherein the ultrasound imaging machine is communicably coupled to a multi-use electronic device for controlling the operation of the ultrasound imaging machine, and wherein the determining whether the at least one first ultrasound image generated in the first imaging mode is for viewing comprises determining whether the multi-use electronic device is actively operated.

14. The method of claim 13, wherein the determining whether the multi-use electronic device is actively operated comprises at least one of: measuring interaction with a user interface of the multi-use electronic device, and measuring multi-use electronic device motion.

15. An ultrasound imaging machine, comprising a processor and a memory storing instructions for execution by the processor, wherein when the instructions are executed by the processor, the ultrasound imaging machine is configured to:
   operate the ultrasound imaging machine in a first imaging mode to generate at least one first ultrasound image, wherein the first imaging mode consumes power at a first power level;
   determine whether the at least one first ultrasound image generated in the first imaging mode is for viewing;
   if determined that the at least one first ultrasound image generated in the first imaging mode is not for viewing, change from the first imaging mode to a second imaging mode that consumes power at a second power level, wherein the second power level is lower than the first power level;
   operate the ultrasound imaging machine in the second imaging mode to generate at least one second ultrasound image;
   determine whether the at least one second ultrasound image generated in the second imaging mode is for viewing; and
   if determined that the at least one second ultrasound image generated in the second imaging mode is not for viewing, change from a second imaging mode to a freeze mode that consumes power at a third level, wherein the third power level is lower than the second power level.

16. The ultrasound imaging machine of claim 15, wherein when determining whether the at least one first ultrasound image generated in the first imaging mode is for viewing, the ultrasound imaging machine is further configured to determine if the ultrasound imaging machine has been inactive for longer than a first time period, and wherein when determining whether the at least one second ultrasound image generated in the second imaging mode is not for viewing, the ultrasound imaging machine is further configured to determine if the ultrasound imaging machine has been inactive for longer than a second time period.

17. A multi-use electronic device for controlling operation of an ultrasound imaging machine, the multi-use electronic device comprising a processor and a memory storing instructions for execution by the processor, wherein when the instructions are executed by the processor, the multi-use electronic device is configured to:
   command the ultrasound imaging machine to operate in a first imaging mode, wherein the first imaging mode consumes power at a first power level;
   determine whether the multi-use electronic device is actively operated; and
   if determined that the multi-use electronic device is not actively operated, transmit information to the ultrasound imaging machine indicating that the multi-use electronic device is not actively operated;
   wherein based on the indication, the ultrasound imaging machine changes from the first imaging mode to a second imaging mode that consumes power at a second power level, wherein the second power level is lower than the first power level.

18. The multi-use electronic device of claim 17, wherein if the multi-use electronic display device continues to not be actively operated, the multi-use electronic device is further configured to:
   transmit further information to the ultrasound imaging machine to indicate that the multi-use electronic device continues to not be actively operated;
   wherein based on the further information, the ultrasound imaging machine changes from a second imaging mode to a freeze mode that consumes power at a third level, wherein the third power level is lower than the second power level.

19. The multi-use electronic device of claim 17, wherein the determining whether the multi-use electronic device is actively operated comprises at least one of:
   measuring interaction with a user interface of the multi-use electronic device, and
   measuring multi-use electronic device motion.

20. The multi-use electronic device of claim 19, wherein the measuring of multi-use electronic device motion is performed by a motion sensor on the multi-use electronic device.

* * * * *